(12) United States Patent
Sekitani et al.

(10) Patent No.: US 11,883,200 B2
(45) Date of Patent: Jan. 30, 2024

(54) BIOSIGNAL MEASUREMENT APPARATUS

(71) Applicant: OSAKA UNIVERSITY, Suita (JP)

(72) Inventors: Tsuyoshi Sekitani, Suita (JP); Takafumi Uemura, Suita (JP); Teppei Araki, Suita (JP); Shusuke Yoshimoto, Suita (JP)

(73) Assignee: Osaka University, Osaka (JP)

( * ) Notice: Subject to any disclaimer, the term of this patent is extended or adjusted under 35 U.S.C. 154(b) by 85 days.

(21) Appl. No.: 17/588,028

(22) Filed: Jan. 28, 2022

(65) Prior Publication Data
US 2022/0142577 A1 May 12, 2022

Related U.S. Application Data

(63) Continuation of application No. 16/069,503, filed as application No. PCT/JP2016/073112 on Aug. 5, 2016, now Pat. No. 11,234,645.

(30) Foreign Application Priority Data

Jan. 12, 2016 (JP) ................................. 2016-003958

(51) Int. Cl.
*A61B 5/00* (2006.01)
*A61B 5/25* (2021.01)
(Continued)

(52) U.S. Cl.
CPC .......... *A61B 5/6833* (2013.01); *A61B 5/0002* (2013.01); *A61B 5/25* (2021.01);
(Continued)

(58) Field of Classification Search
CPC ... A61B 5/0002; A61B 5/0006; A61B 5/0022; A61B 5/0205; A61B 5/25; A61B 5/291;
(Continued)

(56) References Cited

U.S. PATENT DOCUMENTS

| 9,579,055 B1 | 2/2017 | Rood et al. |
| 2004/0030258 A1 | 2/2004 | Williams et al. |

(Continued)

FOREIGN PATENT DOCUMENTS

| AU | 2011254054 A1 | 1/2012 |
| JP | H 7-275217 A | 10/1995 |

(Continued)

OTHER PUBLICATIONS

Extended European Search Report issued in PCT/JP2016073112 dated May 3, 2019.
(Continued)

*Primary Examiner* — Orlando Bousono
(74) *Attorney, Agent, or Firm* — Knobbe, Martens, Olson & Bear, LLP (57) ABSTRACT

A biosignal measurement apparatus is used by being affixed on a living body. The apparatus includes an affixed part that is a sheet, in which a signal-acquiring section of multiple electrodes and wiring connected to each of the electrodes are formed, and which can be freely expanded, contracted and bent and is adhesive; and a substrate that is connected to the wiring and on which a signal-processing circuit for wirelessly transmitting biosignals obtained through the wiring is mounted. The signal-acquiring section is exposed on the surface of the affixed part and the affixed part and the substrate are stacked so that the back surface of the affixed part faces the substrate.

12 Claims, 6 Drawing Sheets

(51) Int. Cl.
  *A61B 5/291*    (2021.01)
  *A61B 5/296*    (2021.01)
  *A61B 5/369*    (2021.01)
  *A61B 5/318*    (2021.01)
  *A61B 5/389*    (2021.01)
  *A61B 5/398*    (2021.01)

(52) U.S. Cl.
  CPC ............. *A61B 5/291* (2021.01); *A61B 5/296* (2021.01); *A61B 5/369* (2021.01); *A61B 5/6843* (2013.01); *A61B 5/318* (2021.01); *A61B 5/389* (2021.01); *A61B 5/398* (2021.01); *A61B 2503/04* (2013.01); *A61B 2560/0214* (2013.01); *A61B 2562/0209* (2013.01); *A61B 2562/046* (2013.01); *A61B 2562/125* (2013.01); *A61B 2562/164* (2013.01); *A61B 2562/166* (2013.01)

(58) Field of Classification Search
  CPC ......... A61B 5/282; A61B 5/296; A61B 5/318; A61B 5/369; A61B 5/389; A61B 5/398; A61B 5/6823; A61B 5/6833; A61B 5/6843; A61B 2503/04; A61B 2560/0214; A61B 2562/0209; A61B 2562/046; A61B 2562/125; A61B 2562/164; A61B 2562/166

See application file for complete search history.

(56) References Cited

U.S. PATENT DOCUMENTS

| | | | |
|---|---|---|---|
| 2007/0123756 A1 | 5/2007 | Kitajima et al. | |
| 2008/0139953 A1* | 6/2008 | Baker ................ | A61B 5/14542 600/509 |
| 2009/0062670 A1* | 3/2009 | Sterling ................ | G06Q 10/10 600/509 |
| 2011/0166491 A1 | 7/2011 | Sankai | |
| 2011/0237922 A1* | 9/2011 | Parker, III ............ | A61B 5/1112 600/382 |
| 2012/0238890 A1* | 9/2012 | Baker .................. | A61B 5/0006 600/509 |
| 2013/0281814 A1 | 10/2013 | Tilt et al. | |
| 2014/0100432 A1 | 4/2014 | Golda et al. | |
| 2014/0100467 A1* | 4/2014 | Baker .................. | A61B 5/0006 600/509 |
| 2014/0243694 A1* | 8/2014 | Baker .................. | A61B 5/0006 600/509 |
| 2014/0249385 A1 | 9/2014 | Wada et al. | |
| 2015/0126848 A1* | 5/2015 | Baker .................... | A61B 5/301 600/391 |
| 2015/0257647 A1 | 9/2015 | Buck et al. | |
| 2016/0029917 A1 | 2/2016 | Baker et al. | |
| 2016/0029918 A1 | 2/2016 | Baker et al. | |
| 2016/0066808 A1 | 3/2016 | Hijazi | |

FOREIGN PATENT DOCUMENTS

| | | |
|---|---|---|
| JP | 2001-212092 A | 8/2001 |
| JP | 2007-125104 A | 5/2007 |
| JP | 2013-85621 A | 5/2013 |
| JP | 2014-505529 A | 3/2014 |
| WO | WO 2009/055415 A2 | 4/2009 |
| WO | WO 2010/029966 A1 | 3/2010 |

OTHER PUBLICATIONS

The Nikkei Shimbun, Nov. 30, 2015.
Nihon Kohden, Products, Neurology, available online at https://eu.nihonkohden.com/en/products/neurology, accessed May 14, 2018.
Nihon Kohden, Products, Cardiology, available online at https://eu.nihonkohden.com/en/products/cardiology, accessed May 14, 2018.
Office Action received in Japanese Patent Application No. 2017-561508 dated Aug. 20, 2019.
Office Action issued in the EP Patent Application No. EP16884982.6, dated Dec. 16, 2019.

* cited by examiner

BIOSIGNAL MEASUREMENT APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to an apparatus for measuring a potential variation with time with an electrode, such as electrical activity in a living body.

Description of the Related Art

The potential variation generated accompanying activity in a living body, such as brain waves and an electrocardiogram, is measurable via an electrode attached to the outside of the living body. In a hospital, a research institute and the like, the potential variation measured in such a manner is conventionally used as a biosignal to noninvasively grasp the presence or absence of abnormality and the degree thereof in a living body. An apparatus for the measurement, that is, an examination instrument for medical use or for research use such as an electroencephalograph or an electrocardiograph, is downsized as with consumer apparatus. Such an examination instrument is required to have high precision, and is used in a consultation room or an examination room of medical facilities, a visit destination or the like to a subject who is in a state of low activity, in many cases. Therefore, even a downsized examination instrument, for example, an electroencephalograph, is formed to have such a size and weight as to have portability to the extent of being movable when the instrument not in use is set on a base with a caster or stored in a dedicated case (refer to Non-Patent Document 1).

On the other hand, a portable size electrocardiograph is available, and is configured with a main body of a rigid housing, and a plurality of cables each which extends from the main body or is connected to the main body, and which has an electrode at the tip thereof (refer to Non-Patent Document 2).

Non-Patent Document 1

Physiological examination equipment: electroencephalograph, produced by Nihon Kohden Corporation, [online] Dec. 8, 2015, [Searched on Jan. 5, 2016], Website (URL: http://www.nihonkohden.co.jp/iryo/products/physio/03_eeg/index.html)

Non-Patent Document 2

Physiological examination equipment: electrocardiograph, produced by Nihon Kohden Corporation, [online] Dec. 25, 2015 [Searched on Jan. 5, 2016], Website (URL: http://www.nihonkohden.co.jp/iryo/products/physio/01_ecg/index.html)

SUMMARY OF THE INVENTION

Problems to be Solved by the Invention

Examination by a conventional examination instrument gives not much physical burden on a subject, if the examination is carried out for a relatively short period of time at a specific place as described above. However, the burden may be inappropriately large in some cases depending on the purpose of an examination or on a subject.

As a specific example, an examination for acquiring a biosignal during sleep is considered below. A plurality of electrodes to be worn, an application agent applied at a portion on which the electrodes are worn, contact to the skin of the cables connecting the electrodes and the main body, and the like impart strong wearing feeling or uncomfortable feeling to a subject to disturb the onset of sleep of the subject, or affect electrical activity occurring in the subject's body. As a result, biosignal of the subject during normal sleep is not acquired. It may be difficult to perform the examination, especially in some cases where a subject who has a low anti-stress property such as an infant or a young child or a subject who has insufficient control ability of the body show large body response against the wearing feeling and/or the uncomfortable feeling.

A conventional electroencephalograph restricts the motion of a subject by the cables, whereby the situations where measurement can be performed are limited. In an example, monitoring with measurement is not available with respect to a biosignal of a subject who takes daily action.

Furthermore, the examination by the examination instrument as described above is performed in a relatively large scale. The measurement of brain waves is basically difficult to be performed by a patient or patient's family member at home, unlike a simple examination with a stethoscope, a sphygmomanometer, a clinical thermometer or the like, and thus needs to be performed in medical facilities. A portable electrocardiograph is usable at home, but is limited in performance such as due to the number of channels. Therefore, a biosignal of a patient even not in a serious situation may need to be measured in medical facilities, thereby requiring not only the physical burden on the patient (subject) described above, but also a time burden and a financial burden on both of the subject and the medical facilities.

The present invention has been made in view of these problems. The object of the present invention is to provide a biosignal measurement apparatus for combining ease of measurement and high performance with less wearing feeling and less uncomfortable feeling imparted to a subject.

Means for Solving the Problems

The biosignal measurement apparatus according to the present invention, which is provided to achieve the above-described object, is a biosignal measurement apparatus to be used by being affixed on a living body. The biosignal measurement apparatus includes a sheet which is formed with a plurality of electrodes and a plurality of wirings connected to the plurality of electrodes respectively, and which is freely expanded, contracted and bent, and is adhesive, and a substrate which is connected to the plurality of wirings and equipped with a signal processing circuit for wirelessly transmitting a biosignal acquired via the plurality of wirings. The plurality of electrodes are exposed on a front surface of the sheet, and the sheet and the substrate are stacked so that a back surface of the sheet faces the substrate.

The plurality of electrodes included in the biosignal measurement apparatus are affixed together with the sheet which is affixable like a poultice, on the living body. Therefore, an application agent is not required, and no cable is in contact with the skin. Since the affixed sheet and the electrodes follow the shape and motion of the affixed portion of the living body, the sheet and the electrodes are hardly displaced and hardly peel off from the affixed portion. The biosignal measurement apparatus is configured so that the substrate and the sheet are stacked to be compactly assembled as a whole, and has no cable restricting the motion of the subject, thereby hardly imparting wearing feeling and uncomfortable feeling to the subject.

In such a biosignal measurement apparatus, each of the sheet and the substrate under the state of the front surface of the sheet affixed on the living body may have an outer shape in plan view of a size falling within a rectangle of 5 cm×15 cm.

This provides the biosignal measurement apparatus which has the entire size falling within the forehead of a subject and is capable of measuring the brain waves of the subject.

The plurality of electrodes may include a reference electrode and a plurality of measurement electrodes.

This allows measurement of a potential variation based on a reference potential acquired within the range of the affixed portion, as a biosignal with multiple channels.

The reference electrode may be affixed on the sheet in an aspect of being attachable to and detachable from the sheet.

This allows, for example, a medical staff member to use the biosignal measurement apparatus to carry out the measurement method based on the same principle as that of the biosignal measurement method which has been conventionally carried out. Therefore, the medical staff member feels less operation resistance to this biosignal measurement apparatus even if the shape and size are different from those of a conventional apparatus. The biosignal acquired by use of the biosignal measurement apparatus is used with the same feeling as the signal acquired by a conventional apparatus.

The plurality of electrodes may include some electrodes arranged parallelly in at least two rows, and each of the rows may include a plurality of electrodes in line.

This allows the biosignal to be continuously measured at the affixed portion, even if some of the electrodes are peeled off from the skin.

The sheet may have a flexible connecting part. The plurality of wirings may extend respectively and correspondingly from the electrodes to the connecting part. The connecting part may be bent so that the sheet is folded back, and a tip of the connecting part may be connected to the signal processing circuit.

This allows the substrate including the signal processing circuit and the sheet including the electrodes and the wirings to be arranged so as to be folded back and stacked, thereby enabling to provide the entire biosignal measurement apparatus in a smaller size in plan view.

The connecting part of the sheet may be configured so as to increase in hardness from a portion close to the plurality of electrodes toward a portion close to the tip.

This prevents stress from concentrating at the tip portion of the sheet connected to the substrate, thereby enabling to prolong the service life of the sheet.

The signal processing circuit may include an analog circuit for processing an analog signal acquired via the plurality of electrodes to convert the analog signal into a digital signal, a digital circuit for processing the digital signal acquired by the analog circuit to transmit the digital signal wirelessly, and a power source circuit for supplying power to the analog circuit and the digital circuit. The analog circuit, the digital circuit and the power source circuit may be respectively mounted in a first region, a second region and a third region obtained by dividing a mounting surface of the substrate into three regions.

This suppresses noise coming in between the analog circuit and the digital circuit.

The analog circuit may have an A/D converting section for converting the analog signal into a digital signal having a bit number of 20 bits or more.

This allows measurement with high resolution comparable to a conventional biosignal measurement apparatus.

The analog circuit may have a contact state-detecting circuit for detecting a contact state between the plurality of electrodes and the living body by measuring a contact impedance between the plurality of electrodes and the living body.

This makes it possible to confirm the contact state between the electrodes and the skin of the subject, thereby ensuring and maintaining the wearing state in which appropriate measurement is available.

The power source circuit may include a rechargeable battery, a connection terminal provided on the substrate, and a charging circuit for charging the battery with power supplied through the connection terminal.

This allows the biosignal measurement apparatus to be used as a wearable measurement apparatus worn by the subject.

It is noted that the generic or specific aspects may be realized by a system, an integrated circuit, a computer program, or a recording medium such as a computer-readable CD-ROM, or may be realized by an arbitrary combination among a system, an integrated circuit, a computer program and a recording medium.

Effects of the Invention

The present invention provides a biosignal measurement apparatus for combining ease of measurement and precision with less wearing feeling and less uncomfortable feeling imparted to a subject.

DETAILED DESCRIPTION OF THE PREFERRED EMBODIMENT

Some embodiments will be specifically described below with reference to the drawings.

It is noted that each of the embodiments described below represents a comprehensive or specific example. Numerical values, shapes, materials, constituent elements, arrangement positions and connection configurations of the constituent elements, and the like indicated in the following embodiments are mere examples, not intended to limit the present invention. Among the constituent elements in the following embodiments, the constituent elements not described in the independent claims each meaning the highest order concept are described as arbitrary constituent elements.

Embodiment

[1. Overall Configuration]

Figure 1:
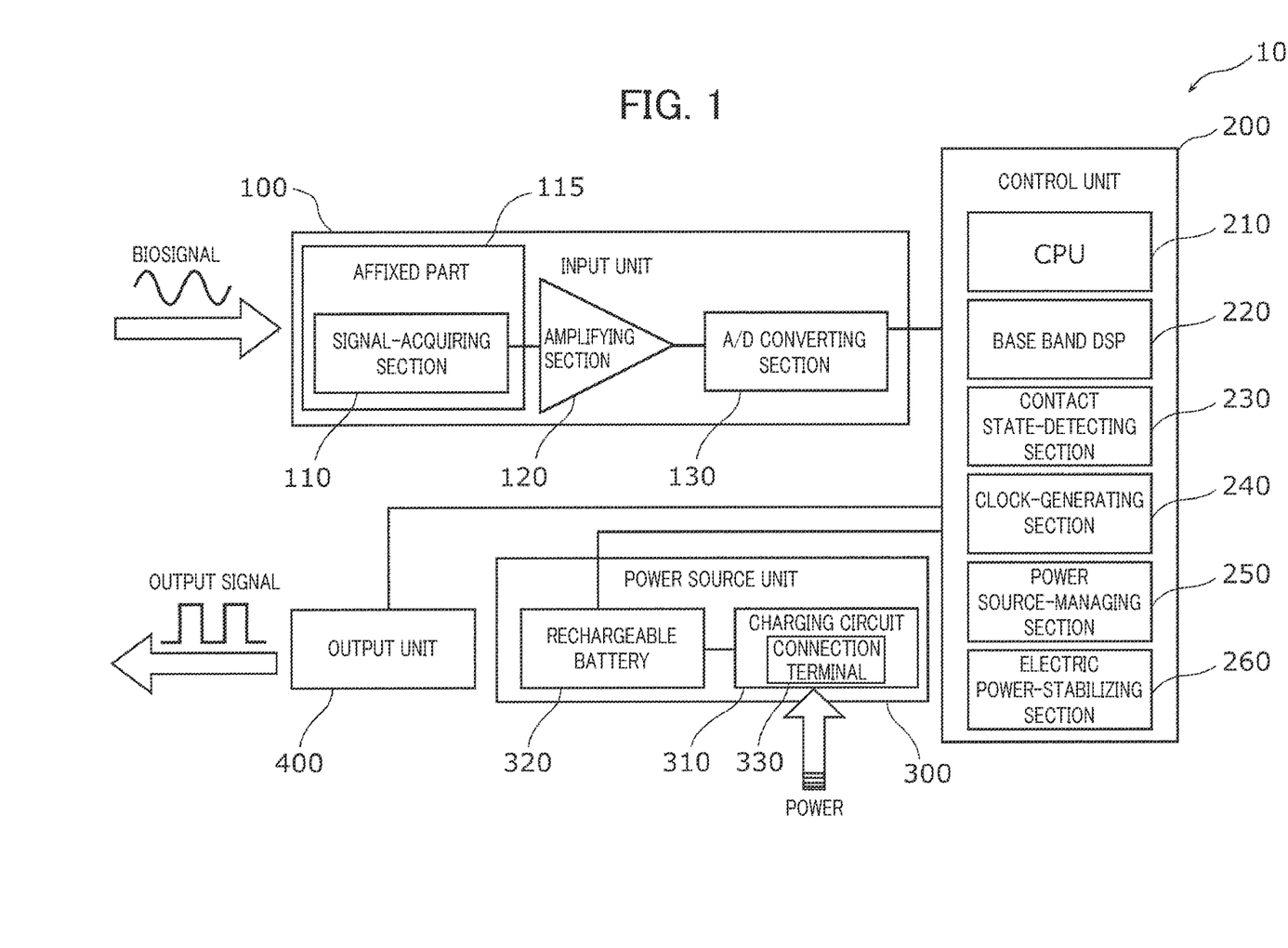
FIG. 1 is a block diagram illustrating the outline of the configuration of a biosignal measurement apparatus according to an embodiment of the present invention.

FIG. 1 is a block diagram illustrating the outline of the configuration of a biosignal measurement apparatus 10 according to the present embodiment.

The biosignal measurement apparatus 10 is an apparatus for measuring a potential variation with time occurring in a living body with an electrode to acquire it as a biosignal, and outputting data on the biosignal. The potential variation in a living body herein is the minute potential variation (several tens of microvolts to several tens of millivolts) occurring by the activity of, for example, brain, heart or other muscle.

The biosignal measurement apparatus 10 includes an input unit 100, a control unit 200, a power source unit 300, and an output unit 400. The physical arrangement of these constituent elements will be described below by use of examples.

The input unit 100 measures a detectable potential in a living body via the skin of the living body, and outputs a signal indicating a time series variation of the measured potential to the control unit 200. The input unit 100 includes a signal-acquiring section 110, an affixed part 115, an amplifying section 120, and an analog-to-digital converting section (hereinafter and in FIG. 1, also referred to as an A/D converting section) 130.

The signal-acquiring section 110, which is of multiple thin film electrodes, is formed so as to be exposed on one surface of the affixed part 115 which is an adhesive sheet. In the following description, the surface side of the affixed part 115 on which the signal-acquiring section 110 is exposed is also referred to as the front surface of the affixed part 115, while the opposite surface is also referred to as the back surface. The affixed part 115 is affixed on a living body such that the front surface thereof comes into contact with the skin of the living body. The signal-acquiring section 110 detects a potential under such a state. The potential of each of the multiple electrodes of the signal-acquiring section 110 is measurable. The biosignal acquired by measuring the potential with each of the electrodes is input to the control unit 200 via the amplifying section 120 and the A/D converting section 130 through an individual transmission path (channel). It is noted that these electrodes include one or more reference electrodes and one or more measurement electrodes, and the biosignal is acquired in such a manner that the potential difference between each measurement electrode and the reference electrode corresponding to the measurement electrode is measured.

Each of the signal-acquiring section 110 and the affixed part 115 has expandability and contractibility, and flexibility allowing free bending, and thus follows, when affixed on the body surface of a subject, the shape and motion of the affixed portion thereof.

As an example, an adhesive base material is used as the affixed part 115 having such characteristics, made of a silicone material for use as a base material such as of a poultice. The affixed part 115 made of such material has high moisture permeability in addition to high expandability and contractibility and high flexibility, thereby enabling to suppress the subject from feeling uncomfortable and sweating during wearing. Such material also has high biocompatibility, whereby the affixed part 115 is capable of being worn for a long period.

The signal-acquiring section 110 of multiple electrodes may be made of an expandable and contractible conductor using metal particles. In addition, wiring, which is formed on the affixed part 115 so as to transmit a signal from the signal-acquiring section 110 to the outside of the affixed part 115, may be made of the expandable and contractible conductor. The electrodes and wiring made of the expandable and contractible conductor are capable of expanding up to approx. 700%. Silver nanowire, for example, may serve as the metal particles, whereby a conductivity of approx. 10000 S/cm is acquired. Accordingly, the biosignal of a subject is input to the amplifying section 120 described below through the electrodes and wiring having low resistance and low noise. That is, each of the signal-acquiring section 110 and the wiring, which are made of the expandable and contractible conductor, combines expandability and contractibility, preferable transparency, and conductivity, and its expandability disturbs no motion of a subject.

The affixed part 115 on which the signal-acquiring section 110 and wiring are formed is a sheet which is freely expanded, contracted and bent as a whole and is adhesive, and which is capable of being worn for a long period.

It is noted that in the signal-acquiring section 110, the expandable and contractible conductor made of metal particles may not be exposed on the front surface of the affixed part 115. In an example, the signal-acquiring section 110 may be configured with a conductive gel material and the expandable and contractible conductor stacked in layers, wherein the gel material may be exposed on the front surface of the affixed part 115, while the expandable and contractible conductor may be embedded in the affixed part 115. This suppresses the deterioration of the expandable and contractible conductor caused by oxidation of metal particles or the like, and also makes the biosignal measurement apparatus 10 according to the present embodiment available even to a subject having allergy to metal.

The amplifying section 120 amplifies the biosignal input by the signal-acquiring section 110, and outputs the signal to the A/D converting section 130. The amplifying section 120 may be realized as, for example, an amplifying circuit including an operational amplifier on a substrate described below.

The A/D converting section 130 converts into a digital signal the biosignal which is an analog signal input by the amplifying section 120, and outputs the signal to the control unit 200. It is noted that in order to obtain precision (resolution) comparable to that of a conventional medical instrument, the A/D converting section 130 of the biosignal measurement apparatus 10 according to the present embodiment is realized by an A/D converting section for converting an analog signal into a digital signal having a bit number of 20 bits or more. For example, a 24-bit ΔΣ type A/D converter is used.

The control unit 200 controls the entire operation of the biosignal measurement apparatus 10. The control unit 200 includes a central processing unit (hereinafter also referred to as CPU, and indicated as CPU in FIG. 1) 210, a base band digital signal processor (hereinafter also referred to as a base band DSP, and indicated as DSP in FIG. 1) 220, a contact state-detecting section 230, a clock-generating section 240, a power source-managing section 250, and an electric power-stabilizing section 260.

The CPU 210 reads out and executes a program from a storage section (not shown) to manage and control operation of each of the constituent elements included in the biosignal measurement apparatus 10.

The base band DSP 220 performs predetermined processing on the digital signal input by the input unit 100, and then outputs the digital signal to the outside via the output unit 400.

The contact state-detecting section 230 is an electronic circuit (a contact state-detecting circuit) for detecting a contact state between the living body and the signal-acquiring section 110 of electrodes. Specifically, the contact state-detecting section 230 measures a contact impedance between the signal-acquiring section 110 and the skin of the living body, and determines whether the contact state is good or poor on the basis of the magnitude of the contact impedance. The determination is made during, for example, wearing and measurement of the biosignal, thereby ensuring the proper wearing state of the biosignal measurement apparatus 10. It is noted that the criterion for determining that the contact state is poor may be changed as appropriate through setting. In the case where the input unit 100 has 8 channels of signal input paths, as an example, the contact state may be determined poor when even one channel of an electrode out of the eight channels is detected as being disconnected (in a lead-off state) from the subject. Alternatively, the contact state may be determined poor when a majority of five channels are detected each as being in a lead-off state.

The clock-generating section 240 is a clock generating circuit for generating an internal clock of the CPU 210.

The power source-managing section 250 and the electric power-stabilizing section 260, along with the power source unit 300 described below, constitute a power source circuit to supply the power input by the power source unit 300 as the power for driving the control unit 200 and other constituent elements. The power source-managing section 250 includes, for example, a DC-DC converter. The input unit 100 and the output unit 400 respectively receive power having different voltages transformed by the power source-managing section 250. The electric power-stabilizing section 260 is a regulator for stabilizing the power for supplying.

The power source unit 300 supplies the power required for the operation of each of the constituent elements of the biosignal measurement apparatus 10 via the power source-managing section 250 and the electric power-stabilizing section 260 described above. The power source unit 300 includes a charging circuit 310 and a rechargeable battery 320.

The charging circuit 310 is the circuit which, in order to charge the rechargeable battery 320, receives power from the outside of the biosignal measurement apparatus 10 and controls the voltage and current of the received power, thereby supplying the controlled power to the rechargeable battery 320. The charging circuit 310 includes a connection terminal 330 for receiving power. The connection terminal 330 may be, for example, a power receiving terminal for receiving power from a commercial power outlet via a cable, or may be a port such as of a USB (universal serial bus) capable of receiving power from an external apparatus capable of supplying power.

The rechargeable battery 320 is a battery which is capable of being recharged and in which the power to be supplied to each of the constituent elements of the biosignal measurement apparatus 10 is stored. A battery having a capacity according to use application is used as the rechargeable battery 320. In an example, the battery may have a capacity allowing continuous use for a long period of time enough for monitoring a subject in a wakeful state or a sleeping state. The rechargeable battery 320 is realized by, for example, a button type battery or a thin film battery, by taking into consideration the wearing feeling and the like imparted to the subject during use in addition to the capacity. This enables to suppress the increase in weight and size imparting stronger wearing feeling of the biosignal measurement apparatus 10, and the decrease in followability to the shape of the living body.

The output unit 400, which is a wireless communication module capable of wirelessly transmitting data, outputs in real time the biosignal output by the base band DSP 220 to an external apparatus of the biosignal measurement apparatus 10, for example, a storage unit, a display unit such as a monitor, or an information terminal including these. A communication system based on a communication standard, for example, Bluetooth (registered trademark) or Wi-Fi (registered trademark) is used for the output unit 400 in the present embodiment. A low power consumption communication system such as Bluetooth (registered trademark) Low Energy (BLE) may be used, in order to prolong the continuous use period of time of the biosignal measurement apparatus 10. It is noted that since each communication system has an upper limitation in an information amount (transmission rate) for real-time output according to its bandwidth, the sampling rate of the analog signal by the A/D converting section 130 is changed according to the communication system and the number of channels for measurement.

The biosignal measurement apparatus 10 according to the present embodiment having the above-described configuration is used in a manner that the affixed part 115 is affixed on a living body. When used as described above, the biosignal measurement apparatus 10 including the power source unit 300 and the output unit 400 described above are not required to have any power supply cable for constantly supplying power or any communication cable for constantly outputting biosignals. Accordingly, the subject wearing the biosignal measurement apparatus 10 feels no wearing feeling caused by these cables, and is not restricted in motion. Since the use of a plurality of electrodes provides the biosignal measurement apparatus 10 with redundancy, even if a lead-off state occurs due to motion or sweating of the subject, or the like, the biosignal measurement apparatus 10 is capable of monitoring the wearing state on the basis of the detection of the lead-off state. Accordingly, the use of the biosignal measurement apparatus 10 reliably ensures to execute monitoring even over a long period of time, as an example.

The biosignal measurement apparatus 10 having the above-described configuration is further capable of measuring a potential with high precision in a wide dynamic range with 24-bit measurement resolution. Specifically, the biosignal measurement apparatus 10 is capable of acquiring a minute biosignal of 1 µV or less in the measurement range of ±2.5V with resolution of 0.2 µV. The biosignal measurement apparatus 10 as described above has high versatility allowing application to measurement of brain waves, and various types of myoelectric potentials including a cardiac potential and an ocular potential.

[2. Example]

As described above, the biosignal measurement apparatus 10 having the above-described configuration is available as an electroencephalograph, an electrocardiograph, an electromyograph, and the like. The biosignal measurement apparatus 10 used as an electroencephalograph is specifically described below, taking it as an example of the biosignal measurement apparatus 10 according to the present embodiment.

[2-1. Overview]

Figure 2:
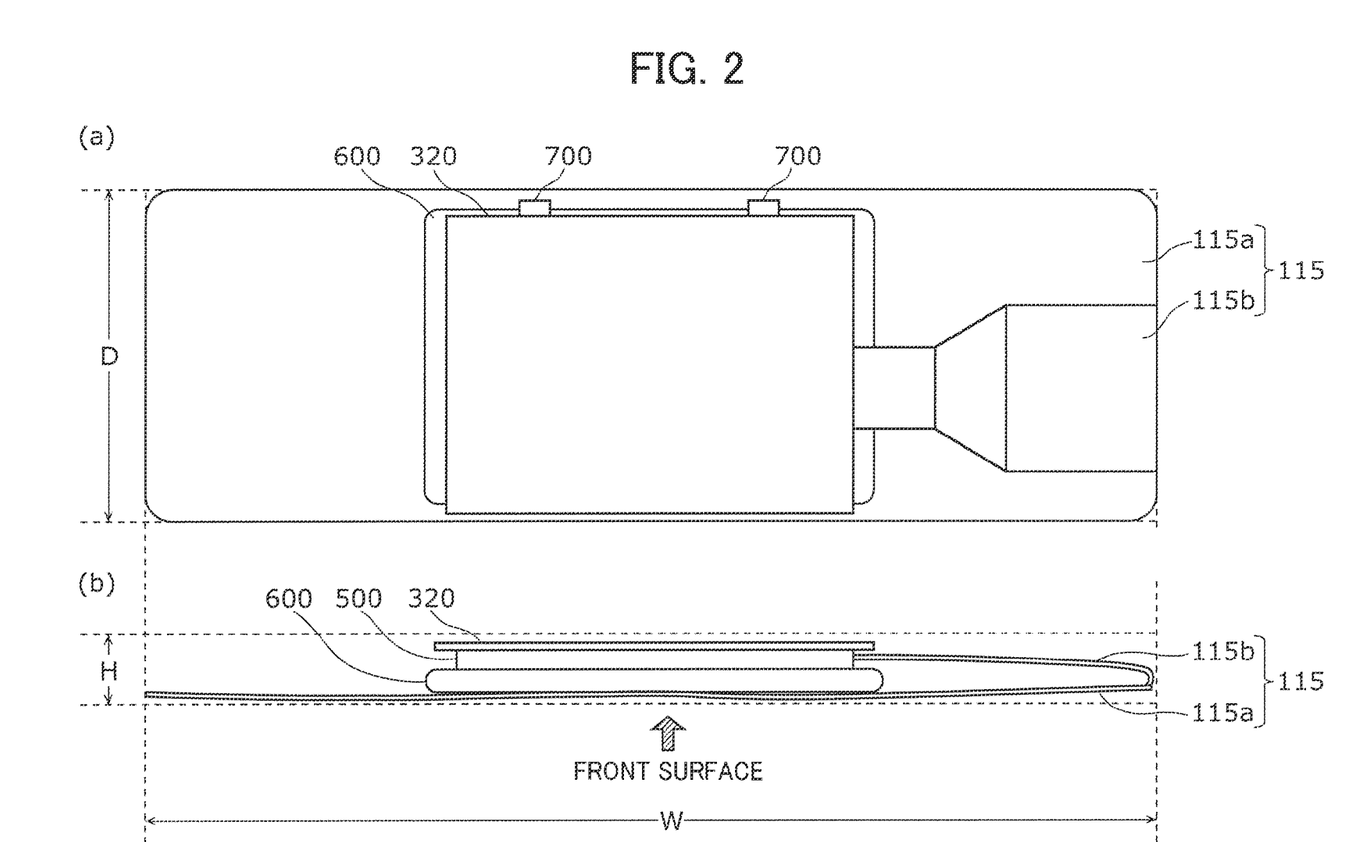
FIG. 2 is a schematic diagram illustrating the appearance of the configuration of the biosignal measurement apparatus used as an electroencephalograph according to an example of the present invention.

FIG. 2 is a schematic diagram illustrating the appearance of the biosignal measurement apparatus 10 used as an electroencephalograph. FIG. 2(a) is a plan view, while FIG. 2(b) is a front view. It is noted that some of the constituent elements shown in FIG. 1 are omitted in FIG. 2 for the sake of ease of viewing. In an example, although the affixed part 115 may be transparent and thus the signal-acquiring section 110 may be visible from the back surface side thereof, the illustration of the signal-acquiring section 110 is omitted in FIG. 2. The lower side in the diagram shown in FIG. 2(b), which corresponds to the front surface, is to be affixed and worn so as to come into contact with the forehead of a subject.

As shown in FIG. 2(a) and FIG. 2(b), the substrate 500 and the rechargeable battery 320 are disposed so as to be stacked on the back surface side (upper side in the figure) of the affixed part 115 in the biosignal measurement apparatus 10 used as an electroencephalograph. The rechargeable battery 320 is connected to the substrate 500 via a cable 700.

In the biosignal measurement apparatus 10 according to the present example, the affixed part 115, which is an adhesive sheet freely expanded, contracted and bent as described above, has a shape and size approximately falling within the forehead of a human, in the plan view shown in FIG. 2(a). It is noted that the affixed part 115 is configured with an affixed part main body 115a and a connecting part 115b which form a series of sheets. The affixed part main body 115a including the signal-acquiring section 110 has a substantially rectangular shape falling within an approximate size of a rectangle having a depth (D in the diagram) of 5 cm and a width (W in the diagram) of 15 cm. In view of the fact that the biosignal measurement apparatus 10 imparting less uncomfortable feeling during wearing is also suitable as an electroencephalograph for an infant, the affixed part main body 115a is designed to have a size falling within the forehead of an infant. It is noted that each of the electrodes of the signal-acquiring section 110 is small enough so that the plurality of electrodes are enabled to be disposed with certain intervals on the affixed part 115 having even such a size. The connecting part 115b includes the wiring (not shown in FIG. 2) extending from the signal-acquiring section 110. The wiring extends to the tip of the connecting part 115b so as to be exposed. When the biosignal measurement apparatus 10 according to the present example is used, the connecting part 115b having flexibility is bent so as to fold back the affixed part 115 having a sheet shape as described above, thereby falling within the size of the above-described rectangle in plan view.

As shown in FIG. 2(b), the substrate 500 is overlaid so as to face the back surface of the affixed part 115. In the present example, the substrate 500 is overlaid on the affixed part 115 via a cushion 600 made of an adhesive gel material. For example, a flexible substrate serves as the substrate 500. Therefore, the substrate 500 along with the above-described cushion 600 provides a certain degree of followability to the shape of the forehead and the motion of the skin or the muscle of the subject wearing the biosignal measurement apparatus 10, resulting in suppressing an uncomfortable feeling during wearing. A circuit (hereinafter also referred to as a signal processing circuit) for processing the biosignal acquired by the signal-acquiring section 110 is mounted on the flexible substrate. The tip of the connecting part 115b is connected to the substrate 500 so that the biosignal acquired by the signal-acquiring section 110 is input to the signal processing circuit through the wiring. The substrate 500 will be detailed below.

The rechargeable battery 320, which is a battery having a flexible sheet shape with a thickness of approx. 1 mm, and which is in a state of being connected to the substrate 500, is overlaid so as to face the substrate 500 as shown in FIG. 2(b). A battery having a capacity according to use application is used. In an example, in the case where the biosignal measurement apparatus 10 is used to monitor a subject during sleep, a battery may be used, having a capacity allowing continuous use for 10 hours or longer, for example, a battery having the capacity of 200 mAh or more if the driving current of the biosignal measurement apparatus 10 is 20 mA.

In the biosignal measurement apparatus 10 according to the present example, the affixed part 115, the cushion 600, the substrate 500, and the rechargeable battery 320 are stacked as described above. In plan view of the biosignal measurement apparatus 10 under such a state, the cushion 600, the substrate 500, and the rechargeable battery all fall within the size of the rectangular shape of the affixed part 115 described above. It is noted that a cable also falling within the size is used as the cable 700 for connecting the substrate 500 and the rechargeable battery 320. The thickness (H in the figure) and weight of the entire biosignal measurement apparatus 10 are also suppressed to the utmost. The suppression of the size and weight as described above enables to impart less wearing feeling and less uncomfortable feeling to the subject wearing the biosignal measurement apparatus 10 on the forehead. In the case where the biosignal measurement apparatus 10 according to the embodiment described above has the configuration of the present example and has the substrate 500 and the rechargeable battery 320 falling within the outer shape of the affixed part 115, the thickness and weight are reduced to the extents not exceeding 7 mm and 25 g, as an example. It is noted that in view of weight reduction, the affixed part 115 including the signal-acquiring section 110 is preferably formed as thin as possible, alternatively, in order to provide strength enough for practical handling, the affixed part 115 may be formed to have an appropriate thickness. In an example, in the case of the affixed part 115 having the size of the present example, the thickness of approx. 1 mm can provide practical strength.

Figure 3:
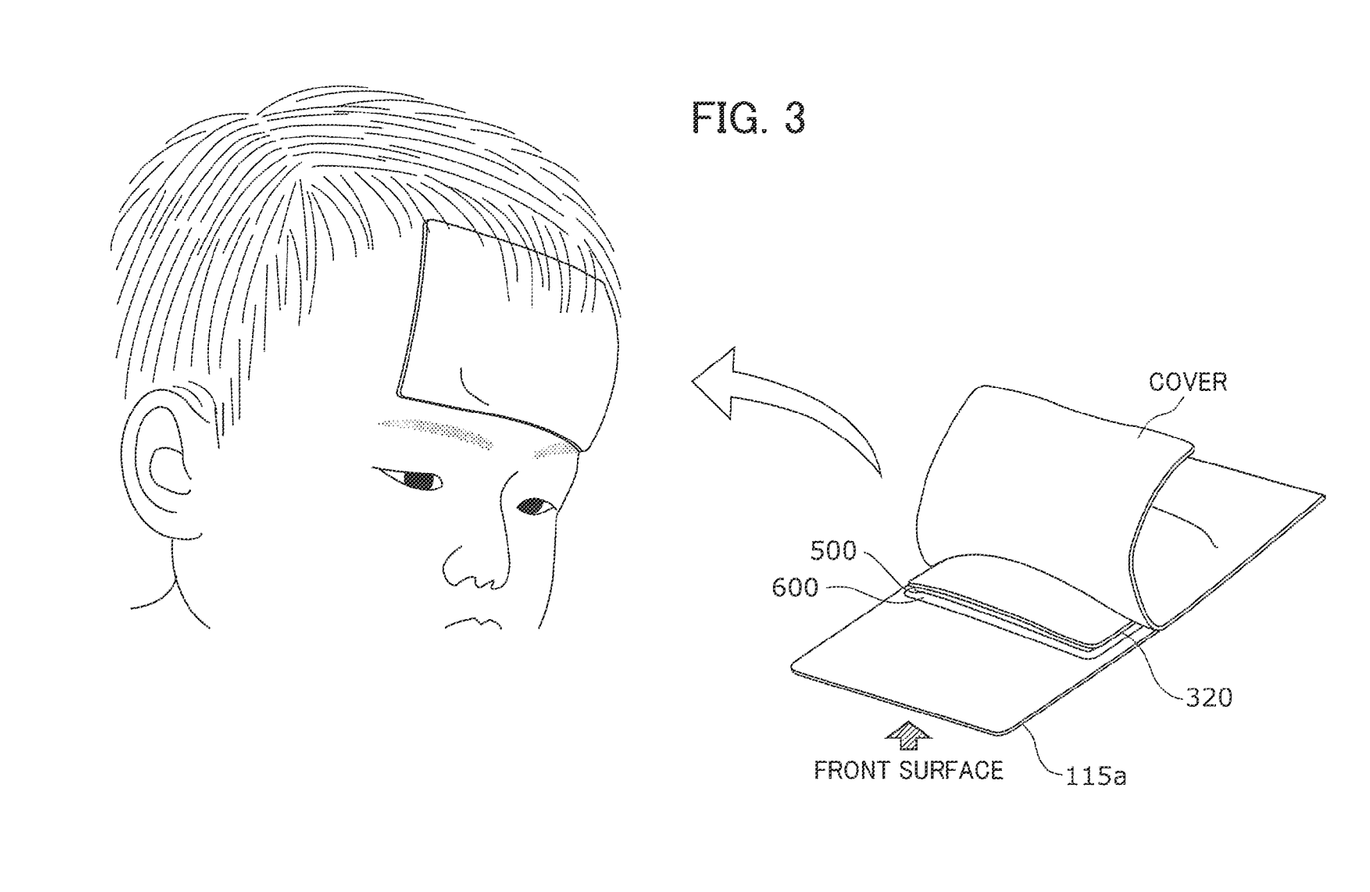
FIG. 3 is a diagram illustrating an example in which a subject wears the biosignal measurement apparatus according to the example of the present invention.

FIG. 3 shows an example in which a subject wears the biosignal measurement apparatus 10 according to the present example. In FIG. 3, the biosignal measurement apparatus 10 further covered with a cover not shown in FIG. 2 over the rechargeable battery 320 is affixed so that the front surface of the affixed part main body 115a comes into contact with the forehead of the subject. As described above, the biosignal measurement apparatus 10 according to the present example is affixed on the forehead, like a commercially available cooling gel sheet. The biosignal measurement apparatus 10 includes no cable and the like extending from the biosignal measurement apparatus 10 to the outside to transmit a signal or supply power, and thus the subject can freely move within a range in which measurement data is wirelessly transmitted to a destination. A mobile information terminal and storage unit, such as a notebook-type personal computer, tablet, and smartphone are used as a transmission destination of the measurement data, thereby enabling to further reduce the restriction in the motion range of the subject.

Electroencephalographs for research use or consumer use are conventionally used, having a simpler configuration compared to electroencephalographs for medical use. In each of these electroencephalographs, the electrodes thereof are fixed to the head of a subject with a fixing tool using elastic resin, rubber or the like. Such a fixing tool has upper and lower restriction in sizes applicable to the head. On the other hand, in the biosignal measurement apparatus 10 according to the present example, the electrodes are enabled to be fixed to the head of a subject without such a fixing tool, and thus the biosignal measurement apparatus 10 is available to, for example, an infant with a small circumference of the head. In the biosignal measurement apparatus 10 according to the present example, the head is not squeezed by a force unlike the case of an elastic fixing tool, and thus the biosignal measurement apparatus 10 is more likely to be used even with, for example, a subject who has injured his/her head, as compared with a conventional electroencephalograph.

[2-2. Affixed Part and Signal-Acquiring Section]

Figure 4:
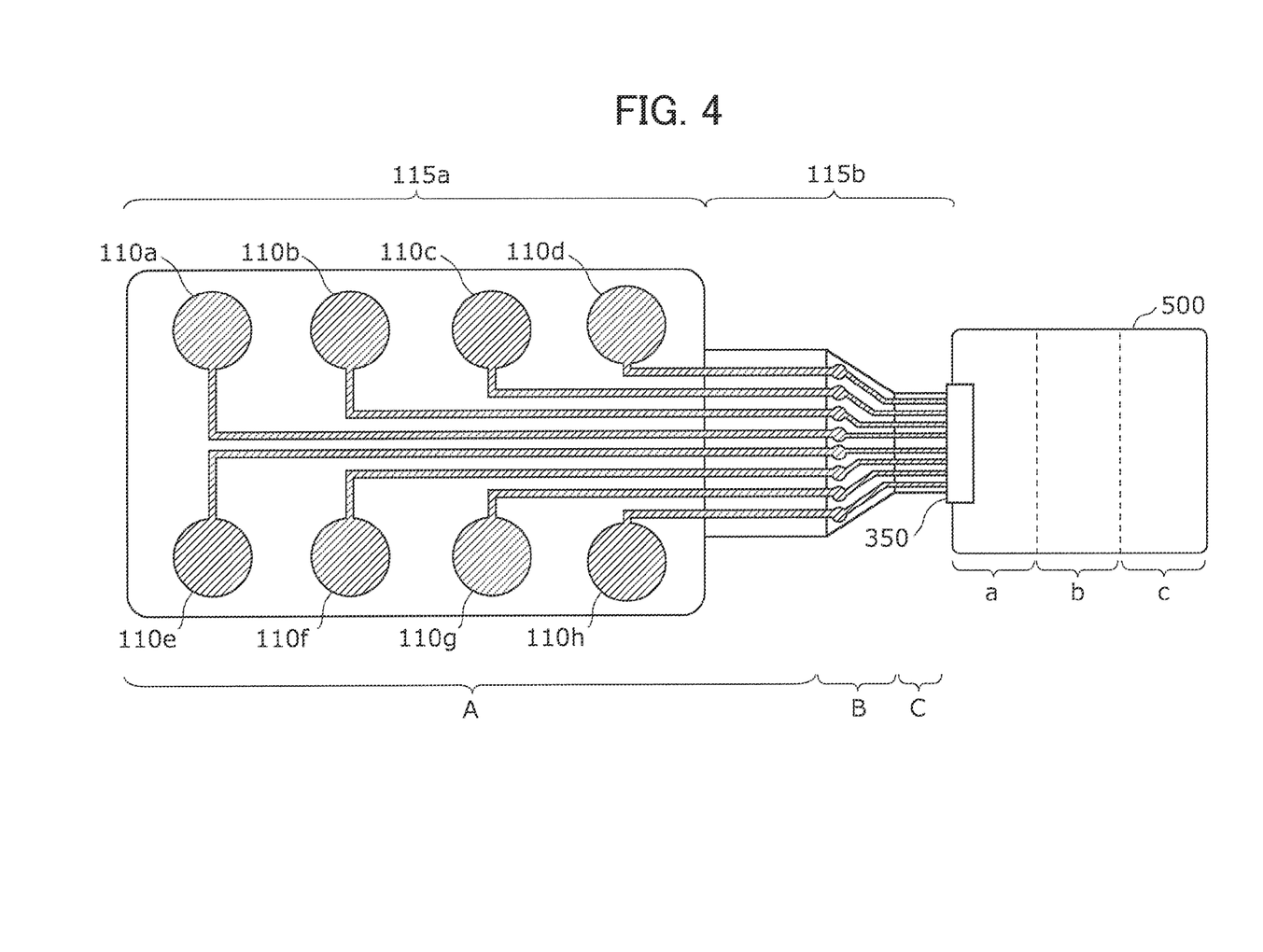
FIG. 4 is a diagram illustrating a configuration example of an affixed part including a signal-acquiring section and a substrate, of the biosignal measurement apparatus according to the example of the present invention.

FIG. 4 is a diagram illustrating a configuration example of the affixed part 115 including the signal-acquiring section 110, and the substrate 500, of the biosignal measurement apparatus 10 according to the present example shown in FIG. 2. FIG. 4 shows that the affixed part 115 and the substrate 500 are in an unfolded state and are connected via a connector 350.

In FIG. 4, the eight hatched circles (110a to 110h) provided in the affixed part main body 115a correspond to the individual electrodes of the signal-acquiring section 110. In the example shown in FIG. 4, the affixed part 115 has two rows which parallelly extend in the longitudinal direction of the affixed part 115, and each which includes four signal-acquiring sections 110 in line. Each of the hatched lines extending from each signal-acquiring section 110 to the right end of the connecting part 115b corresponds to the wiring serving as a path of a biosignal. It is noted that the signal-acquiring section 110 is not limited to the present example in the shape, the number, the number of rows, and the positional relation among the signal-acquiring sections 110. The wiring pattern is not limited to the example shown in FIG. 4.

As described above, these signal-acquiring sections 110 include a reference electrode for acquiring a reference potential, and a measurement electrode for measuring a potential difference from the reference potential at each position. In an example, a signal-acquiring section 110a may be a reference electrode, while a signal-acquiring section 110b may be a measurement electrode for measuring a potential difference from the reference potential acquired by the signal-acquiring section 110a. That is, the signal-acquiring section 110a is the reference electrode to the signal-acquiring section 110b which is a measurement electrode. Similarly, a signal-acquiring section 110c may be the reference electrode to a signal-acquiring section 110d which is a measurement electrode; a signal-acquiring section 110e may be the reference electrode to a signal-acquiring section 110f which is a measurement electrode; and a signal-acquiring section 110g may be the reference electrode to a signal-acquiring section 110h which is a measurement electrode. In this case, the biosignal measurement apparatus 10 is capable of measuring biosignals with four channels. Alternatively, the signal-acquiring section 110a may be the reference electrode to the signal-acquiring sections 110b to 110h which are measurement electrodes. In this case, the biosignal measurement apparatus 10 is capable of measuring biosignals with 7 channels. It is noted that the number of the signal-acquiring sections 110 is not limited to that in the above-described example, and alternatively, biosignals may be measured with more channels by use of more signal-acquiring sections 110.

Figure 5:
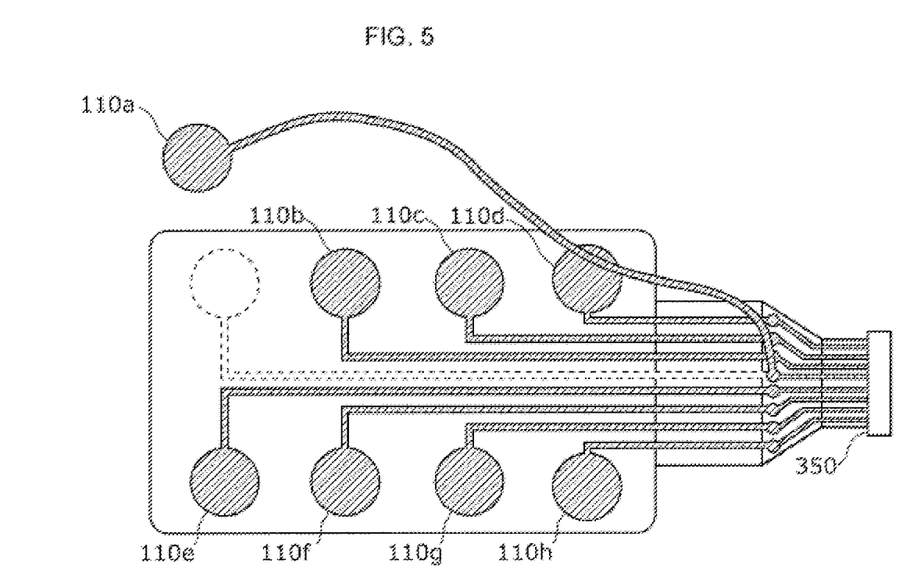
FIG. 5 is a diagram illustrating another configuration example of the affixed part including the signal-acquiring section and the substrate, of the biosignal measurement apparatus according to the example of the present invention.

The plurality of signal-acquiring sections 110 may include an electrode attachable to and detachable from the affixed part 115, and the electrode may be used as a reference electrode for measuring a reference potential at a position other than the forehead, such as the earlobe. As in the example shown in FIG. 5, the signal-acquiring section 110a may be a reference electrode detachable from the affixed part main body 115a. FIG. 5 is a diagram illustrating another example of the configuration of the affixed part 115 including the signal-acquiring section 110, and the substrate 500, of the biosignal measurement apparatus 10 according to the present example shown in FIG. 2. FIG. 5 shows the state where the signal-acquiring section 110a having been affixed on the position indicated by the broken line is peeled off and detached from the affixed part main body 115a. It is noted that the signal-acquiring section 110 detached from the affixed part main body 115a is still in connection with the wiring serving as a path of a signal. The signal-acquiring section 110 once having been peeled off from the affixed part main body 115a as described above is enabled to be affixed again to the affixed part 115 due to the adhesiveness of the affixed part 115.

Although the connecting part 115b has flexibility as described above, the degree of flexibility may be changed depending on the location. In an example, the stress caused by energizing in the routing in the biosignal measurement apparatus 10 and/or by deformation of the connecting part 115b concentrates at the tip portion of the connecting part 115b to be engaged with the connector 350 for connection to the substrate 500. In the case of the connecting part 115b made of flexible material like the affixed part main body 115a, such stress likely breaks the tip portion. In order to prevent such premature breakage, the connecting part 115b as an example may be configured so as to increase in hardness from the portion close to the signal-acquiring section 110 (the affixed part main body 115a) toward the portion close to the tip thereof. In an example, in FIG. 4, an area A, that is, the affixed part main body 115a and a part closer to the affixed part main body 115a of the connecting part 115b, are both made of a flexible silicone material having the above-described expandability and contractibility. An area B next to the area A may be made of a plastic resin which has flexibility of such an extent allowing easy bending and which has lower expandability and contractibility compared to that of the area A. An area C next to the area B including the tip of the connecting part 115b may be made of a plastic resin which has flexibility and lower expandability and contractibility like the area B, and which is harder than the plastic resin of the area B. In such a configuration, the stress as described above is dispersed also to the portions of the boundaries of the materials in the connecting part 115b, not concentrating at the tip portion of the connecting part 115*b*. This delays the breakage of the connecting part 115*b* due to the stress, thereby enabling to prolong the service life of the affixed part 115.

[2-3. Substrate]

The signal processing circuit is mounted on the substrate 500 as described above. The signal processing circuit herein includes the amplifying section 120 and the A/D converting section 130 of the input unit 100, the control unit 200, the charging circuit 310 of the power source unit 300, and the output unit 400. Each of these constituent elements is classified as an analog circuit, a digital circuit or a power source circuit. The analog circuits include the amplifying section 120 and the A/D converting section 130 for processing the analog signal acquired by measuring a potential on the body surface of a living body to convert it into a digital signal. The digital circuits include the CPU 210, the base band DSP 220, the contact state-detecting section 230 and the clock-generating section 240 of the control unit 200, and the output unit 400 for wirelessly transmitting the processed digital signal, which are related to processing of a digital signal. The power source circuits include the power source-managing section 250 and the electric power-stabilizing section 260 of the control unit 200, and the charging circuit 310 and the rechargeable battery 320 of the power source unit 300, which supply power to the analog circuits and the digital circuits. These analog circuits, the digital circuits and the power source circuits are respectively mounted in a first region, a second region and a third region which are obtained by dividing the mounting surface of the substrate 500 into three regions. In an example, in FIG. 4, the area indicated by a is the first region, the area indicated by c is the second region, and the area indicated by b is the third region. The region for the analog circuits is separated from the region for the digital circuits in such a manner, thereby suppressing noise generated on one side from coming into the other side. The voltages of the driving powers are different between the analog circuits and the digital circuits, and thus the output systems from the rechargeable battery 320 are different between the analog circuits and the digital circuits. On the other hand, a GND line is common between the analog circuits and the digital circuits. Accordingly, the region in which the analog circuits are mounted and the region in which the digital circuits are mounted are separated as much as possible in the substrate 500, thereby suppressing the influence by noise.

It is noted that although the shapes and sizes of the respective regions obtained by dividing the substrate 500 are substantially the same in the example shown in FIG. 4, the method of dividing the substrate 500 in the present invention is not limited to that in the present example. The substrate 500 may not be of one physically-continuing sheet of a flexible substrate. In an example, each or some of the first region to the third region may be mounted on a separate flexible substrate, and these flexible substrates may be connected by wiring to transmit a signal and supply power.

The rechargeable battery 320 included in the power source circuits may not be mounted on the substrate 500. In an example, the rechargeable battery 320 may be mounted on the substrate 500 via a holder provided on the substrate 500, or may be connected to a flexible substrate via a cable as shown in FIG. 2.

Although the substrate 500 is a flexible substrate in the case described above, the substrate 500 is not limited to a flexible substrate. That is, the substrate 500 may be a rigid substrate. Even in the case where the substrate 500 is a rigid substrate, the substrate 500 is formed as small as possible in size occupied in the biosignal measurement apparatus 10, whereby less uncomfortable feeling is imparted by the substrate 500 to the subject via the cushion 600 and the affixed part 115.

[2-4. Precision]

The biosignal measurement apparatus 10 according to the present example is rather small and is easily used as compared with a conventional brain wave measuring apparatus for medical use. However, unless the precision in measurement of a biosignal by the apparatus is sufficient, the apparatus is not suitable for use as a medical instrument.

Figure 6A:
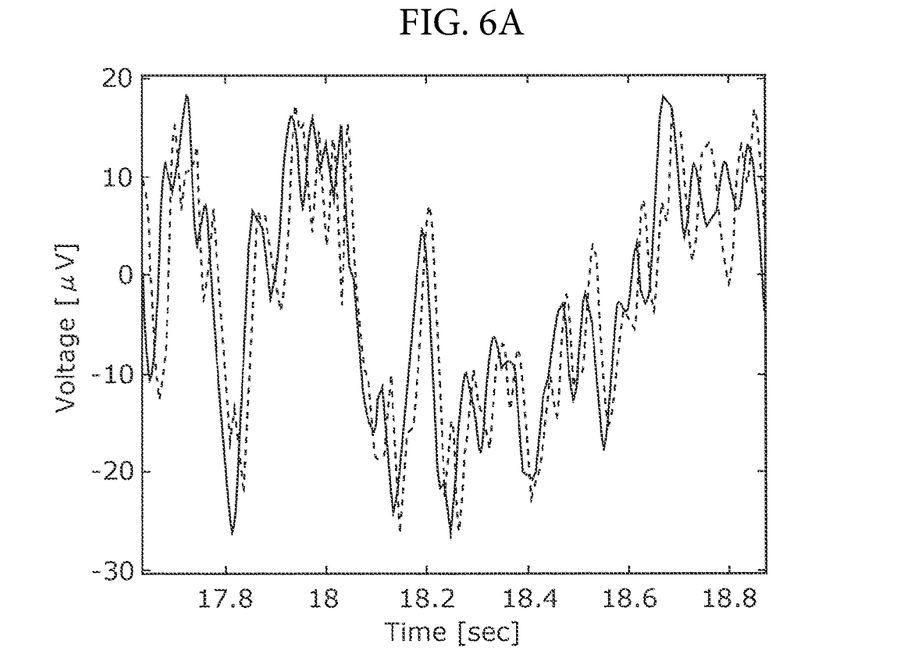
FIG. 6A is a diagram for comparing the brain waves measured by the biosignal measurement apparatus according to the example of the present invention and the brain waves measured by a brain wave measuring apparatus for medical use at the same time.
Figure 6B:
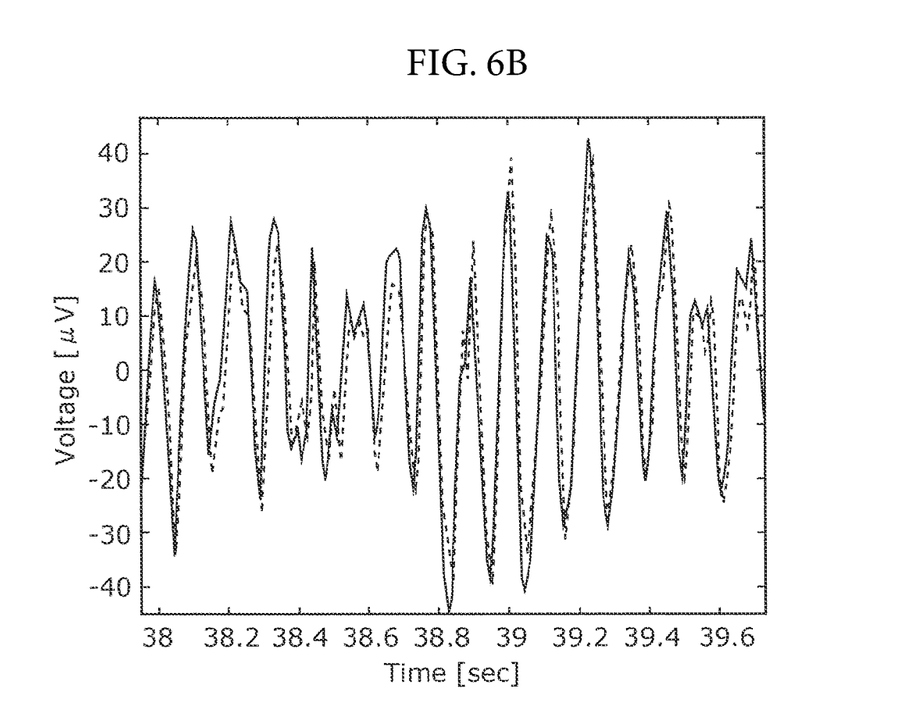
FIG. 6B is another diagram for comparing the brain waves measured by the biosignal measurement apparatus according to the example of the present invention and the brain waves measured by a brain wave measuring apparatus for medical use at the same time.

FIG. 6A and FIG. 6B are the electroencephalograms obtained by concurrently measuring brain waves of one subject by use of both of the biosignal measurement apparatus 10 according to the present example and a brain wave measuring apparatus for medical use (Neurofax (registered trademark) EEG-1200 manufactured by Nihon Kohden Corporation, hereinafter referred to as Neurofax) affixed on the forehead. It is noted that the reference potential is acquired at the earlobe. FIG. 6A shows the electroencephalogram of the brain waves measured in the state where the eyes of the subject are open, while FIG. 6B shows the electroencephalogram of the brain waves measured in the state where the eyes of the subject are open. Each of the solid lines in the curves of these electroencephalograms shows the brain waves acquired by the biosignal measurement apparatus 10 according to the present example, while each of the broken lines shows the brain waves acquired by Neurofax. These electroencephalograms reveal that the brain waves acquired by the both apparatuses are consistent with each other at a high level. The results of the frequency analysis of the acquired brain waves also reveal high consistency therebetween, and further reveal that the brain waves acquired by the both apparatuses have high correlation, with a correlation coefficient of 0.99 or more. As described above, the biosignal measurement apparatus 10 according to the present example is capable of measuring a minute potential variation, for example, brain waves with precision comparable to that of a brain wave measuring apparatus for medical use.

[2-5. Application Example]

The biosignal measurement apparatus 10 according to the present example for use as an electroencephalograph is capable of measuring brain waves with ease and less burden on a wearing subject as compared with a conventional electroencephalograph for medical use or other use. A subject wearing the biosignal measurement apparatus 10 can move and work in some degree. That is, the biosignal measurement apparatus 10 allows continuous measuring of brain waves under a state close to everyday life by using it as a so-called wearable device.

The biosignal measurement apparatus 10 for use as an electroencephalograph as described above is used for, for example, sleep state management at home of a patient of sleep apnea syndrome, quantitative assessment based on brain activity data of ability of the elderly such as in driving or machine work, monitoring and diagnosis by quantitative assessment based on brain activity such as of dementia with abnormal brain activity, Parkinson's disease, epilepsy, psychiatric disorder and the like, monitoring of depth of anesthesia during surgery, research for brain development science, and the like.

In the field of drug discovery, the biosignal measurement apparatus 10 is available for collection of data on the quantitative variation in brain activity caused by administration of medicine for a nervous system. In the field of medical care, the biosignal measurement apparatus 10 is available for collection of data serving as an index for selecting the optimum medicine for a patient from a plurality of medicines having the same purpose.

In the field of nursing care, even in the case of a care receiver having difficulty in communication, the biosignal measurement apparatus 10 is available for monitoring of such a care receiver to detect temperature and discomfort such as pain on the basis of brain waves.

Furthermore, in view of a product to be put to practical use, the biosignal measurement apparatus 10 is expected to be provided at a smaller cost to a subject as compared with a conventional electroencephalograph. This facilitates introduction of the biosignal measurement apparatus 10 to individuals, thereby encouraging the realization of healthcare monitoring aimed at individualized medical care. In some fields other than medical care, the biosignal measurement apparatus 10 is expected to be used by an individual as a user interface of means for controlling a device on the basis of brain waves, means for switching between automatic operation and manual operation for a device on the basis of brain waves, and the like.

[3. Other Application Examples]

In the description of the above examples, the biosignal measurement apparatus 10 is used as an electroencephalograph. Alternatively, as described above, the biosignal measurement apparatus 10 is applicable to an apparatus for measuring a biosignal on the basis of each type of a potential, such as an electrocardiograph, an eye movement electrometer, an electromyograph or the like. The biosignal measurement apparatus 10 is provided also as the above measurement apparatus, imparting less wearing feeling with sufficient precision, as compared with conventional apparatus.

It is noted that the biosignal measurement apparatus 10 provided as such an apparatus for measuring a biosignal other than brain waves has the same basic configuration as that in the above-described embodiment, in which appropriate change is made for adjustment with regard to the number and arrangement of the electrodes serving as the signal-acquiring section 110, the shape and size of the affixed part 115 covering a measurement portion, a processing algorithm for visualizing the acquired biosignals, and the like.

Such a measurement apparatus is available as, for example, an electromyograph at home for a uterus of a pregnant woman for early detection of the timing of a delivery. Such a measurement apparatus is also available as monitoring means in the case where a fetus has abnormality in health condition or as a heart rate meter for a fetus used as a communication tool with the fetus.

The biosignal measurement apparatus 10 is also available for collection of data on body control in sports, rehabilitation, or the like. In such use application, the biosignal measurement apparatus 10 according to the present invention has advantages in imparting less wearing feeling and providing fewer disturbances in exercise, and in having redundancy allowing continuous measurement even under disconnection of some electrodes caused by exercising.

In the case of such use application, the shape and size of the affixed part 115 are not limited to those in the above-described examples, and are appropriately determined in consideration of, for example, the number and arrangement of the signal-acquiring sections 110 according to each use application, and in consideration of the stability of the affixed biosignal measurement apparatus 10 and the wearing feeling imparted to a subject while wearing.

Because wearing feeling is less, the biosignal measurement apparatus 10 is available for simultaneous measurement of brain waves and other biosignals with relatively light burden on a subject by using together with the above-described electroencephalograph.

Although the present invention has been described using embodiments and examples of a biosignal measurement apparatus for a human body, the present invention is applicable to measurement of a potential variation of a living body other than a human body or an object other than a living body. In an example, the variation in potential difference on the surface of a plant is monitored, thereby enabling to control growth of an agricultural crop; and in another example, the potential difference on the surface of a concrete portion of a building is mapped, thereby enabling to detect an internal state, such as regarding whether or not internal corrosion occurs. It is noted that in the case of such use application to an object other than a human body, the shape and size of the affixed part 115 are not limited to those in the above examples, and are appropriately determined, for example, in consideration of the number and arrangement of the signal-acquiring sections 110 according to each use application, and in consideration of the stability of the affixed biosignal measurement apparatus 10.

[4. Modifications]

Although the biosignal measurement apparatus according to the present invention has been described using the embodiments and examples, the present invention is not limited to the above-described embodiments or examples. Modifications made in the biosignal measurement apparatus according to the present invention are described below.

In an example, the above-described biosignal measurement apparatus 10 may not include the cushion 600 provided between the substrate 500 and the affixed part 115. In an example, the substrate 500 may be directly fixed to the affixed part 115, or may be fixed to the cover shown in FIG. 3. The substrate 500 and the affixed part 115 may not be arranged so as to be stacked. In an example, the substrate 500 and the affixed part 115 may be used in an unfolded state as shown in FIG. 4 without being bent at the connecting part.

The biosignal measurement apparatus 10 may further include a storage unit for storing biosignal data. The storage unit is used as, for example, a temporary storage location of data in case where wireless communication with the outside is not available. The data may be output to the outside via the output unit 400 in a state where wireless communication is available. The biosignal measurement apparatus 10 may be configured so that data is output also through an attachable and detachable communication cable. In an example, data may be output through a cable connected to the USB port included in the charging circuit 310.

A power source by environmental power generation using light, vibration or the like may be used additionally, depending on the place or motion of the subject wearing the biosignal measurement apparatus 10, and the use application of the biosignal measurement apparatus. This enables to prolong the continuous use period of time. It is noted that the duration of the battery is adjustable by changing the number of channels, the sampling rate of the analog signal or the like within a range in which measurement data required for each use application is acquired.

The affixed part 115, which is a sheet on which the signal-acquiring section 110 of electrodes and wiring are formed, is made of any material as long as it is freely expanded, contracted and bent and is adhesive as described above, and the material is not limited to silicone. In an example, the affixed part 115 may be a sheet like a courtplaster, made of resin, rubber, fiber (cloth) or other material, or a sheet of a combination thereof having similar characteristics.

The material used for the expandable and contractible conductor of which the signal-acquiring section 110 and wiring are made is not limited to the above-described silver nanowire. Nanowire made of other metal such as gold or copper which are conductors, or carbon nanofiber may be used instead, or a mixture thereof may be used.

The embodiments and the modifications thereof have been described so far as examples for the purpose of explaining the technical contents of the present invention. Accordingly, the technical scope of the invention according to the present application is not limited to the description. The technical scope of the invention according to the present application includes every possible change, replacement, addition, and omission made by those skilled in the art within the range of the specification, drawings and claims, or within the equivalents thereto.

INDUSTRIAL APPLICABILITY

The present invention is applicable to a biosignal measurement apparatus such as an electroencephalograph, an electrocardiograph, an eye movement electrometer, and an electromyograph, and is also applicable to an apparatus for measuring a potential of an object other than a living body, such as of the surface of a building.

EXPLANATION OF REFERENCE NUMERALS

10 BIOSIGNAL MEASUREMENT APPARATUS
100 INPUT UNIT
110, 110A TO 110H SIGNAL-ACQUIRING SECTION
115 AFFIXED PART
115a AFFIXED PART MAIN BODY
115b CONNECTING PART
120 AMPLIFYING SECTION
130 A/D CONVERTING SECTION
200 CONTROL UNIT
210 CPU
220 BASE BAND DSP
230 CONTACT STATE-DETECTING SECTION
240 CLOCK-GENERATING SECTION
250 POWER SOURCE-MANAGING SECTION
260 ELECTRIC POWER-STABILIZING SECTION
300 POWER SOURCE UNIT
310 CHARGING CIRCUIT
320 RECHARGEABLE BATTERY
330 CONNECTION TERMINAL
350 CONNECTOR
400 OUTPUT UNIT
500 SUBSTRATE
600 CUSHION
700 CABLE

What is claimed is:

1. A biosignal measurement apparatus used by being affixed on a living body, the biosignal measurement apparatus comprising:
a sheet formed with a plurality of electrodes and a plurality of wirings connected to the plurality of electrodes respectively, the sheet being freely expanded, contracted and bent and being adhesive, wherein the sheet has a flexible connecting part;
a connector attached to a tip of the flexible connecting part and connected to the plurality of wirings disposed on the sheet; and
a substrate connected to the connector and equipped with a signal processing circuit wirelessly transmitting a biosignal acquired via the plurality of wirings disposed on the connector,
wherein the sheet is physically separated from the substrate, and the sheet is only connected to the substrate via the connector,
wherein the plurality of electrodes are exposed on a front surface of the sheet, and the sheet and the substrate are stacked so that a back surface of the sheet faces the substrate.

2. The biosignal measurement apparatus according to claim 1, wherein
each of the sheet and the substrate under a state of the front surface of the sheet affixed on the living body has an outer shape in plan view of a size falling within a rectangle of 5 cm×15 cm.

3. The biosignal measurement apparatus according to claim 1, wherein
the plurality of electrodes include a reference electrode and a plurality of measurement electrodes.

4. The biosignal measurement apparatus according to claim 3, wherein
the reference electrode is attachable to and detachable from the sheet, and is affixed on the sheet.

5. The biosignal measurement apparatus according to claim 1, wherein
the plurality of electrodes include electrodes arranged parallelly in at least two rows, and each of the rows includes a plurality of electrodes in line.

6. The biosignal measurement apparatus according to claim 1, wherein
the plurality of wirings extend respectively and correspondingly from the electrodes to the connecting part, and
the connecting part is bent so that the sheet is folded back, and a tip of the connecting part is connected to the signal processing circuit.

7. The biosignal measurement apparatus according to claim 6, wherein
the connecting part of the sheet increases in hardness from a portion close to the plurality of electrodes toward a portion close to the tip.

8. The biosignal measurement apparatus according to claim 1, wherein
the signal processing circuit includes an analog circuit for processing an analog signal acquired via the plurality of electrodes to convert the analog signal into a digital signal, a digital circuit for processing the digital signal acquired by the analog circuit to transmit the digital signal wirelessly, and a power source circuit for supplying power to the analog circuit and the digital circuit, and
the analog circuit, the digital circuit and the power source circuit are respectively mounted in a first region, a second region and a third region obtained by dividing a mounting surface of the substrate into three regions.

9. The biosignal measurement apparatus according to claim 8, wherein
the analog circuit has an A/D converting section for converting the analog signal into a digital signal having a bit number of 20 bits or more.

10. The biosignal measurement apparatus according to claim 8, wherein
the analog circuit has a contact state-detecting circuit for detecting a contact state between the plurality of electrodes and the living body by measuring a contact impedance between the plurality of electrodes and the living body.

11. The biosignal measurement apparatus according to claim 8, wherein the power source circuit includes:
a rechargeable battery;
a connection terminal provided on the substrate; and
a charging circuit for charging the battery with power supplied through the connection terminal.

12. The biosignal measurement apparatus according to claim 1, further comprising a cushion between the sheet and the substrate.

* * * * *